US012332237B2

(12) United States Patent
Kanai et al.

(10) Patent No.: US 12,332,237 B2
(45) Date of Patent: Jun. 17, 2025

(54) EXCREMENT DETERMINATION METHOD, EXCREMENT DETERMINATION DEVICE, AND NON-TRANSITORY COMPUTER READABLE RECORDING MEDIUM

(71) Applicant: PANASONIC HOLDINGS CORPORATION, Osaka (JP)

(72) Inventors: Hirofumi Kanai, Osaka (JP); Toshihide Mori, Osaka (JP); Yuka Yamada, Nara (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 229 days.

(21) Appl. No.: 17/986,558

(22) Filed: Nov. 14, 2022

(65) Prior Publication Data

US 2023/0074448 A1 Mar. 9, 2023

Related U.S. Application Data

(63) Continuation of application No. PCT/JP2021/001290, filed on Jan. 15, 2021.
(Continued)

(30) Foreign Application Priority Data

Nov. 5, 2020 (JP) .................. 2020-185250

(51) Int. Cl.
*G01N 33/497* (2006.01)
*A61B 5/00* (2006.01)
*E03D 9/00* (2006.01)

(52) U.S. Cl.
CPC ............. *G01N 33/497* (2013.01); *A61B 5/42* (2013.01); *G01N 33/4975* (2024.05)

(58) Field of Classification Search
CPC ............. G01N 33/0036; G01N 33/497; G01N 33/0054; G01N 33/57419
See application file for complete search history.

(56) References Cited

U.S. PATENT DOCUMENTS 9,671,383 B2* 6/2017 Ansley ................. G01N 33/497
9,947,203 B2* 4/2018 Ansley ................. G01N 27/416
(Continued)

FOREIGN PATENT DOCUMENTS

JP 2015-178764 10/2015
JP 2018-528413 9/2018
(Continued)

OTHER PUBLICATIONS

International Search Report issued in International Pat. Appl. No. PCT/JP2021/001290, dated Mar. 23, 2021, along with an English translation thereof.

*Primary Examiner* — Tran M. Tran
(74) *Attorney, Agent, or Firm* — GREENBLUM & BERNSTEIN, P.L.C.

(57) ABSTRACT

An excrement determination method includes: acquiring sensing data detected by a first gas sensor; acquiring image data captured by a camera; making a first determination of determining whether a gas concentration indicated by the sensing data is higher than a first reference concentration; making a second determination of executing image processing onto the image data and determining whether the image data contains an image about defecation; making a third determination of determining, based on a determination result of the first determination and a determination result of the second determination, that at least one of the defecation and flatulating occurred; and outputting a determination result of the third determination.

10 Claims, 9 Drawing Sheets

Related U.S. Application Data

(60) Provisional application No. 63/030,528, filed on May 27, 2020.

(56) References Cited

U.S. PATENT DOCUMENTS

| | | | | |
|---|---|---|---|---|
| 10,376,246 | B2* | 8/2019 | Kashyap | E03D 11/13 |
| 10,408,818 | B2* | 9/2019 | Bezemer | A47K 13/24 |
| 10,446,008 | B2* | 10/2019 | Ansley | G01N 33/497 |
| 10,571,470 | B2* | 2/2020 | Hasegawa | G01N 33/0062 |
| 10,744,042 | B2* | 8/2020 | Park | G01D 21/02 |
| 11,538,590 | B2* | 12/2022 | Nishiyama | G01N 33/497 |
| 11,819,198 | B2* | 11/2023 | Sekine | G01N 21/84 |
| 12,061,184 | B2* | 8/2024 | Nakamura | G01N 1/24 |
| 12,089,822 | B2* | 9/2024 | Kashyap | H04N 25/76 |
| 2015/0359522 | A1* | 12/2015 | Recht | G01N 21/255 |
| | | | | 600/573 |
| 2016/0223518 | A1* | 8/2016 | Yamaya | G01N 33/497 |
| 2016/0223519 | A1* | 8/2016 | Yamaya | G01N 33/497 |
| 2016/0223548 | A1* | 8/2016 | Kizuka | A61B 5/42 |
| 2016/0223549 | A1* | 8/2016 | Kizuka | G01N 33/0059 |
| 2016/0223550 | A1* | 8/2016 | Hasegawa | A61B 5/4255 |
| 2016/0223551 | A1* | 8/2016 | Kizuka | G01N 33/005 |
| 2016/0223552 | A1* | 8/2016 | Kizuka | G01N 33/004 |
| 2017/0303901 | A1* | 10/2017 | Sekine | G01N 21/84 |
| 2017/0307512 | A1* | 10/2017 | Akagawa | G01N 33/493 |
| 2018/0184906 | A1 | 7/2018 | Prokopp | |
| 2018/0303466 | A1* | 10/2018 | Kashyap | G01N 33/493 |
| 2019/0298316 | A1 | 10/2019 | Kashyap et al. | |
| 2020/0150122 | A1* | 5/2020 | Hasegawa | G01N 33/005 |
| 2022/0211354 | A1 | 7/2022 | Kashyap et al. | |
| 2023/0268041 | A1* | 8/2023 | Grady | G16H 50/20 |
| | | | | 705/2 |
| 2024/0068915 | A1* | 2/2024 | Ishida | G01N 1/24 |
| 2024/0412836 | A1* | 12/2024 | Grady | G06F 3/0482 |

FOREIGN PATENT DOCUMENTS

| | | |
|---|---|---|
| WO | 2018/187790 | 10/2018 |
| WO | 2018/203565 | 11/2018 |

* cited by examiner

EXCREMENT DETERMINATION METHOD, EXCREMENT DETERMINATION DEVICE, AND NON-TRANSITORY COMPUTER READABLE RECORDING MEDIUM

TECHNICAL FIELD

This disclosure relates to a technology of determining excrement excreted from a person.

BACKGROUND ART

Objective management of excrement for care receivers has been recently demanded in care facilities. Patent Literature 1 discloses a technology of determining whether excrement excreted in a bowl part corresponds to one of stool, urine, or wind in accordance with a combination of a determination result as to whether temperature data measured by a temperature measurement part exceeds a temperature threshold and a determination result as to whether odor data measured by an odor measurement part exceeds an odor threshold.

Meanwhile, some people do not generate sufficient odors at defecation or flatulating. Therefore, the technology of Patent Literature 1 using the temperature data and the odor data has a drawback of inaccurate determination as to whether at least one of defecation and flatulating occurred for these people. Moreover, the technology of Patent Literature 1 fails to mention detection of defecation accompanied by flatulating.

CITATION LIST

Patent Literature

Patent Literature 1: Japanese Unexamined Patent Publication No. 2015-178764

SUMMARY OF INVENTION

This disclosure has been achieved to solve the drawback described above, and has an object of providing a technology of making an accurate determination as to whether at least one of defecation and flatulating occurred even for a person who does not generate a sufficient odor at the defecation or the flatulating.

An excrement determination method according to an aspect of this disclosure is used for an excrement determination device that determines excrement. The excrement determination method includes: acquiring sensing data detected by a gas sensor arranged in a toilet room; acquiring image data captured by a camera which is located at a toilet provided in the toilet room to capture an image of a bowl of the toilet; making a first determination of determining whether a gas concentration indicated by the sensing data is higher than a reference concentration; making a second determination of executing image processing onto the image data and determining whether the image data contains an image about defecation; making a third determination of determining, based on a determination result of the first determination and a determination result of the second determination, that at least one of the defecation and flatulating occurred; and outputting a determination result of the third determination.

According to this disclosure, an accurate determination can be made as to whether at least one of defecation and flatulating occurred even for a person who does not generate a sufficient odor at the defecation or the flatulating.

DESCRIPTION OF EMBODIMENTS

Figure 1:
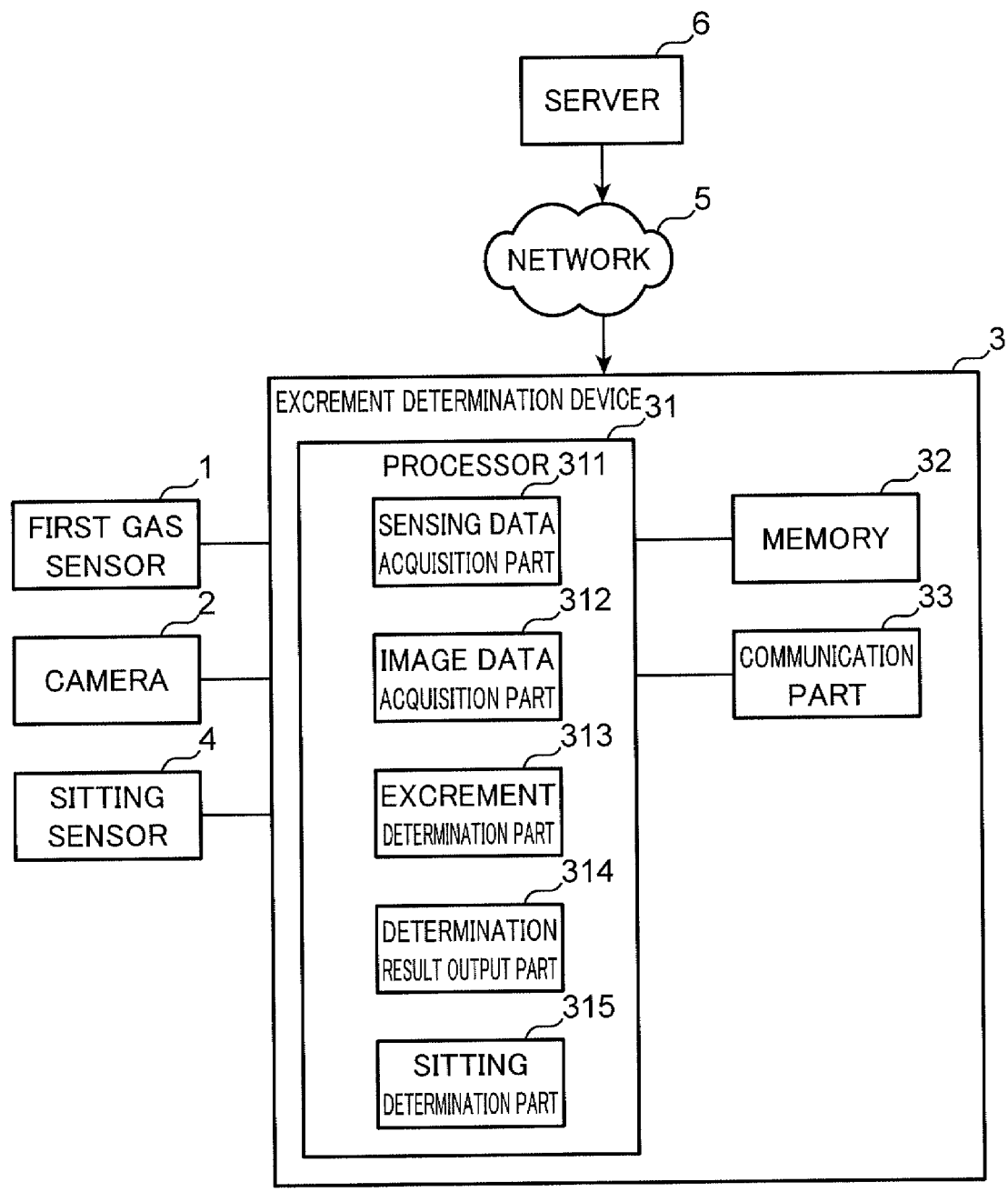
FIG. 1 shows a configuration of an excretion management system in a first embodiment of the disclosure.

Hereinafter, the embodiments of this disclosure will be described with reference to the accompanying drawings. It should be noted that each of the following embodiments illustrates one specific example of the this disclosure, and does not delimit the protection scope of the this disclosure.

Circumstances Led up to this Disclosure

Excretion history information about a frequency and a time of each excretion of defecation, urination, and flatulating is important to grasp a possible health risk of a person. In particular, a care facility accommodating many elderly people who tend to have constipation demands objective recordation of excretion history information about care receivers to cause each of the care receivers to appropriately take a medicine like a laxative. However, such a care facility accommodates a large number of care receivers. Hence, the recordation of the excretion history information by caregivers or carers results in increasing the burden on the caregivers, and thus is not easy for them. Under the circumstances, the present inventors have advanced their studies on the technology of automatically managing excretion history information without human labor.

Aforementioned Patent Literature 1 discloses the relevant technology as a prior art. In Patent Literature 1, in a case where a value of temperature data indicating a temperature of a bowl part of a toilet is larger than a temperature threshold, it is determined that defecation occurred when a value of first odor data measured by a hydrogen sulfide sensor or second odor data measured by an ammonia sensor is larger than an odor threshold, and further determines that urination occurred when both the values of the first odor data and the second odor data are equal to or smaller than the odor threshold. Besides, in Patent Literature 1, in a case where the value of temperature data is equal to or smaller than the temperature threshold, it is determined that flatulating occurred when the value of the first odor data or the second odor data is larger than the odor threshold.

However, some of the people each daily taking a medicine, such as a laxative and an antibiotic, do not generate sufficient odors at defecation or flatulating. In particular, some care receivers tend to each take the aforementioned medicine in a large amount, and are highly unlikely to generate sufficient odors at defecation. Moreover, others may not generate sufficient odors at defecation or flatulating, depending on taken contents of meals. In this regard, Patent Literature 1 has another drawback of an inaccurate determination as to whether defecation occurred for these people.

Specifically, in application of the technology of Patent Literature 1 to each of the people, no temperature change is seen in the bowl part and a measured value of each of the first odor data and the second data is equal to or smaller than the odor threshold at the flatulating. Hence, a determination on the flatulating is failed. Moreover, a measured value of each of the first odor data and the second odor data is equal to or smaller than the odor threshold while a temperature change is seen in the bowl part at the defecation. Therefore, a determination on the defecation is failed. In addition, Patent Literature 1 fails to mention any determination on defecation accompanied by flatulating.

The present inventors have obtained the knowledge that even a person who does not generate a sufficient odor at defecation or flatulating generates odorless gas from an inside of a body of the person. The inventors have further obtained the knowledge that a combination of an analysis result of image data containing a captured image of an inner state of a bowl and an analysis result of sensing data measured by a gas sensor leads to an accurate determination as to whether at least one of the defecation and the flatulating occurred even for such a person who does not generate a sufficient odor at the defecation or the flatulating. Finally, the inventors have conceived of the following aspects of the disclosure in view of the knowledges.

An excrement determination method according to one aspect of this disclosure is used for an excrement determination device that determines excrement. The excrement determination method includes: acquiring sensing data detected by a gas sensor arranged in a toilet room; acquiring image data captured by a camera which is located at a toilet provided in the toilet room to capture an image of a bowl of the toilet; making a first determination of determining whether a gas concentration indicated by the sensing data is higher than a reference concentration; making a second determination of executing image processing onto the image data and determining whether the image data contains an image about defecation; making a third determination of determining, based on a determination result of the first determination and a determination result of the second determination, that at least one of the defecation and flatulating occurred; and outputting a determination result of the third determination.

According to this configuration, it is determined that at least one of the defecation and the flatulating occurred, based on the determination result of the first determination of determining whether the gas concentration detected by the gas sensor is higher than the reference concentration and the determination result of the second determination of determining whether the image data captured by the camera contains the image about the defecation. This configuration therefore enables an accurate determination as to whether at least one of the defecation and the flatulating occurred even for a person who does not generate a sufficient odor at the defecation or the flatulating.

In the excrement determination method, it may be determined in the third determination that the defecation and the flatulating occurred when the determination result of the first determination shows that the gas concentration is higher than the reference concentration and the determination result of the second determination shows that the image data contains an image about the defecation.

According to this configuration, it is determined that the defecation and the flatulating occurred when the determination result of the second determination shows that the image data contains an image about the defecation and the determination result of the first determination shows that the gas concentration detected by the gas sensor is higher than the reference concentration. This configuration therefore enables an accurate determination on the occurrence of the defecation accompanied by the flatulating.

In the excrement determination method, it may be determined in the third determination that the flatulating solely occurred when the determination result of the first determination shows that the gas concentration is higher than the reference concentration and the determination result of the second determination shows that the image data does not contain the image about the defecation.

According to the configuration, it is determined that the flatulating solely occurred when the determination result of the first determination shows that the gas concentration detected by the gas sensor is higher than the reference concentration and the determination result of the second determination shows that the image data does not contain the image about the defecation. This configuration therefore enables an accurate determination on the sole occurrence of the flatulating.

In the excrement determination method, the gas sensor may include a first gas sensor having a sensitivity to hydrogen.

It has been found that even a person who generates no odor discharges hydrogen at the defecation and the flatulating. This configuration includes the first gas sensor having a sensitivity to the hydrogen, and thus enables an accurate determination on the occurrence of at least one of the defecation and the flatulating even for the person who generates no odor at the defecation or the flatulating.

In the excrement determination method, the second determination may be executed when the first determination is affirmative.

This configuration permits the camera to be activated when the first determination is affirmative, and thus eliminates the necessity of making the camera be always active, resulting in reducing power consumption.

In the excrement determination method, the gas sensor may include a first gas sensor having a sensitivity to hydrogen, a second gas sensor having a sensitivity to ammonia, and a third gas sensor having a sensitivity to hydrogen sulfide. The method may further include executing a fourth determination of determining, based on an ammonia concentration detected by the second gas sensor and a hydrogen sulfide concentration detected by the third gas sensor, whether the defecation or urination occurred when the determination result of the first determination shows that the gas concentration detected by the first gas sensor is equal to or lower than the reference concentration.

According to this configuration, it is determined as to whether one of the defecation and the urination occurred, based on the ammonia concentration detected by the second gas sensor and the hydrogen sulfide concentration detected by the third gas sensor, when the first gas sensor fails to detect a hydrogen concentration which is equal to or higher than the reference concentration. This configuration therefore achieves detection of urination which is less detectable by the first gas sensor.

The excrement determination method may further include executing a fourth determination of determining, based on the image data, whether the defecation or urination occurred when the determination result of the first determination shows that the gas concentration detected by the first gas sensor is equal to or lower than the reference concentration.

According to this configuration, it is determined, based on the image data, whether the defecation or the urination occurred when the first gas sensor fails to detect hydrogen having a concentration which is equal to or higher than the reference concentration. This configuration therefore achieves detection of urination which is less detectable by the first gas sensor.

In the excrement determination method, the first determination, the second determination, and the third determination may be executed when it is detected by a sitting sensor for detecting sitting of an excreter on the toilet that the excreter sits on the toilet.

According to this configuration, the first determination, the second determination, and the third determination are made only at the sitting of the excreter, and hence the burden of process on the excrement determination device is reduced.

The excrement determination method may further include: in the output, generating excretion history information including a determination result, daily time information about a date and time when excretion occurred, and the gas concentration, and storing the excretion history information in a memory; determining whether an increase rate of the gas concentration indicated by the excretion history information is equal to or larger than a second threshold when the excretion history information stored in the memory indicates that a defecation interval is equal to or larger than a first threshold and indicates that the flatulating continuously occurred in the defecation interval, and determining that the excreter has constipation when it is determined that the increase rate is equal to or larger than the second threshold; and outputting a determination result of the constipation.

In the constipation, the frequency of flatulating increases as the defecation interval increases. Moreover, the gas concentration of the gas excreted from the inside of the body increases due to the flatulating in the constipation. According to this configuration, a determination on the constipation is made, when the defecation interval is equal to or larger than the first threshold and occurrence of continuous flatulating in the defecation interval are specified from excretion history information, and further an increase rate of the gas concentration changes by the second threshold or larger. This configuration therefore enables an accurate determination on the constipation.

The excrement determination method may further include: in the output, generating excretion history information including a determination result, daily time information about a date and time when excretion occurred, and the gas concentration, and storing the excretion history information in a memory; calculating, based on the excretion history information stored in the memory, an increase rate of the gas concentration, and determining, based on whether the increase rate is equal to or larger than a third threshold, a medication state of the excreter; and outputting a determination result of the medication state.

It has been found that suspension of the intake of the medicine prescribed for the excreter results in an increase in the gas concentration of the gas excreted from the inside of the body when at least one of the defecation and the flatulating occurred. According to this configuration, the increase rate of the gas concentration is calculated, based on the excretion history information, and the medication state of the excreter is determined, based on whether the increase rate is equal to or larger than the third threshold. This configuration therefore achieves an accurate determination on the medication state of the intake or no intake of the medicine by the excreter.

An excrement determination device according to another aspect of the disclosure is an excrement determination device that determines excrement. The excrement determination device includes: a sensing data acquisition part that acquires sensing data from a gas sensor arranged in a toilet room; an image data acquisition part that acquires image data from a camera which is located at a toilet provided in the toilet room to capture an image of a bowl of the toilet; an excrement determination part that makes a first determination of determining whether a gas concentration indicated by the sensing data is higher than a reference concentration, a second determination of executing image processing onto the image data and determining whether the image data contains an image about defecation, and a third determination of determining, based on a determination result of the first determination and a determination result of the second determination, that at least one of the defecation and the flatulating occurred; and a determination result output part that outputs the determination result of the third determination.

An excrement determination program according to further another aspect of the disclosure causes a computer to: acquire sensing data from a gas sensor arranged in a toilet room; acquire image data from a camera which is located at a toilet provided in the toilet room to capture an image of a bowl of the toilet; execute a first determination of determining whether a gas concentration indicated by the sensing data is higher than a reference concentration; execute a second determination of executing image processing onto the image data and determining whether the image data contains an image about defecation; execute a third determination of determining, based on a determination result of the first determination and a determination result of the second determination, that at least one of the defecation and flatulating occurred; and output a determination result of the third determination.

These configurations exert the same effects as those of the excrement determination method described above.

This disclosure can be realized as: an excrement determination program for causing a computer to execute each distinctive feature included in such an excrement determination method; or an excrement determination device including the distinctive feature. Additionally, it goes without saying that the computer program is distributable as a non-transitory computer readable storage medium like a CD-ROM, or distributable via a communication network like the Internet. Each of the embodiments which will be described below represents a specific example of the disclosure. Numeric values, shapes, constituent elements, steps, and the order of the steps described below are mere examples, and thus should not be construed to delimit the disclosure. Moreover, constituent elements which are not recited in the independent claims each showing the broadest concept among the constituent elements in the embodiments are described as selectable constituent elements. The respective contents are combinable with each other in all the embodiments.

First Embodiment

Figure 2:
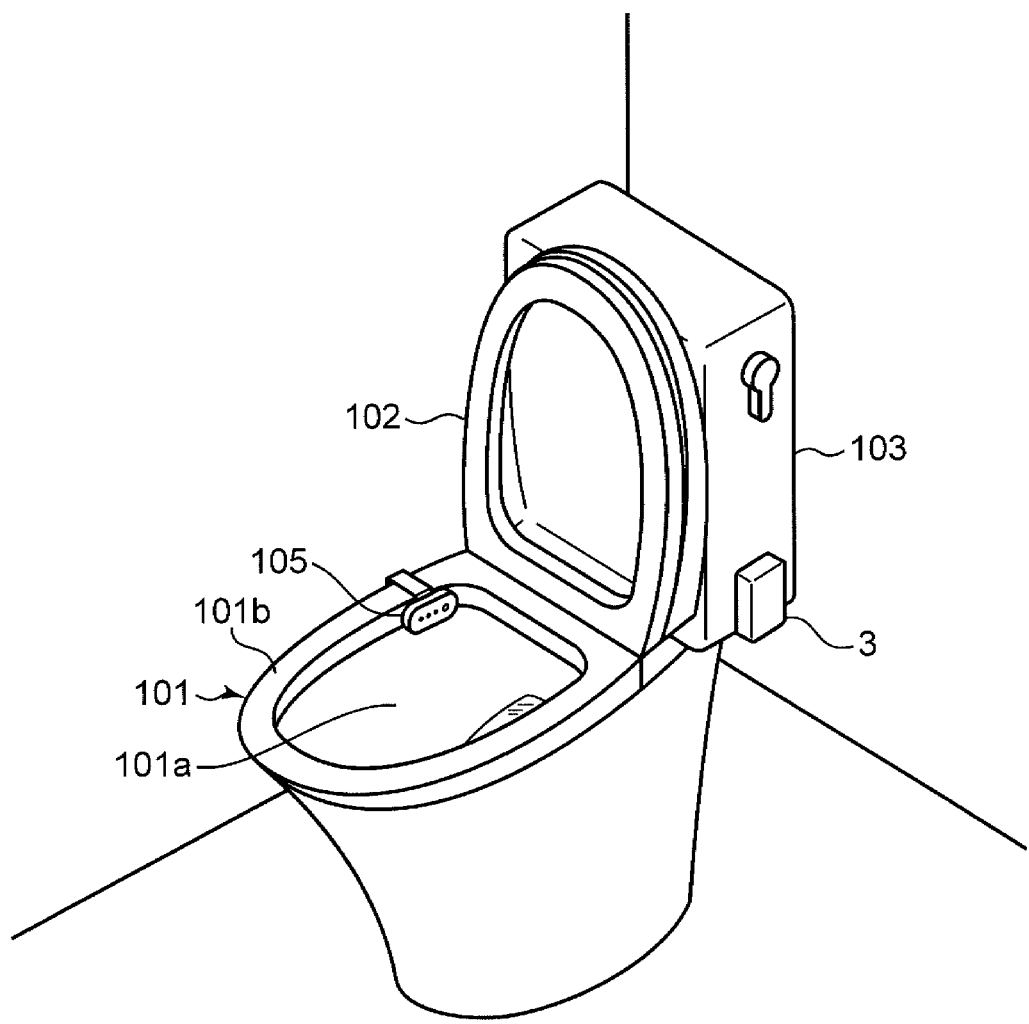
FIG. 2 is a view explaining arrangement positions of a sensor unit and an excrement determination device in the first embodiment of the disclosure.

FIG. 1 shows a configuration of an excretion management system in a first embodiment of the disclosure. FIG. 2 is a view explaining arrangement positions of a sensor unit 105 and an excrement determination device 3 in the first embodiment of the disclosure. In the following description, excrement includes stool, urine, and wind.

The excretion management system shown in FIG. 1 includes a first gas sensor 1, a camera 2, the excrement determination device 3, a sitting sensor 4, and a server 6. The first gas sensor 1 is located in a toilet 101 and has a sensitivity to hydrogen. The first gas sensor 1 is arranged inside the sensor unit 105 shown in FIG. 2. As shown in FIG. 2, the toilet 101 includes a bowl 101a and a fringe part 101b. The fringe part 101b is located at a top end of the toilet 101 and defines an opening section. The bowl 101a is located below the fringe part 101b to receive stool and urine. The sensor unit 105 is attached on the fringe part 101b. The first gas sensor 1 detects a hydrogen concentration in a space in the toilet 101. The first gas sensor 1 is communicably connected to the excrement determination device 3 through a wireless or wired communication therebetween. The first gas sensor 1 transmits sensing data indicating the detected hydrogen concentration to the excrement determination device 3. The first gas sensor 1 may be arranged outside the sensor unit 105 without limitation to the inside of the sensor unit 105. For instance, the first gas sensor 1 may be provided on a peripheral wall of the toilet 101, or may be provided in any position in a toilet room.

The bowl 101a has a bottom provided with an unillustrated drainage channel. The stool and the urine excreted in the bowl 101a flow out through the drainage channel. Moreover, a toilet seat 102 is provided on a top of the toilet 101 to allow an excreter to sit thereon. The toilet seat 102 is rotatable upward and downward. The excreter sits on the toilet seat 102 lowered to lie on the toilet 101. A water reservoir tank 103 that stores water to cause the stool and urine to flow is provided in the rear of the toilet 101.

The first gas sensor 1 may transmit, to the excrement determination device 3, sensing data indicating the hydrogen concentration as detected in a period from a time point when the excreter sits on the toilet seat 102 to a time point when the excreter leaves the toilet seat 102. However, this is a mere example, and the first gas sensor 1 may always transmit, to the excrement determination device 3, sensing data indicating a detected hydrogen concentration.

The camera 2 is located at the toilet 101 to capture an image of the bowl 101a. Here, the camera 2 is arranged in the sensor unit 105. For instance, the camera 2 has a high sensitivity and a wide angle, and is configured to capture a color image having an R (red) component, a G (green) component, and a B (blue) component. A camera for capturing an image of a target by irradiating the target with an infrared light emitting diode and a white light emitting diode is universally used in a field of detecting objects. However, such a conventional camera faces difficulty in detecting, in particular, a target having many red-based color components. Therefore, it is difficult to distinguish stool and urine from each other. From this perspective, a camera having a high sensitivity and a wide angle is adopted as the camera 2 in the embodiment. Specifically, the camera 2 includes a CMOS having a size of one fourth inch with a high sensitivity. The camera 2 is in the form of a wide-angle camera having a horizontal view angle of 120 degrees and a vertical view angle of 45 degrees. The numeral value of each of the inches and the angles shows a mere example, and another numerical value is adoptable. The camera 2 is communicably connected to the excrement determination device 3 through a wireless or wired communication therebetween. The camera 2 captures an image of an inner portion of the bowl 101a at a predetermined frame rate, and transmits obtained image data. Here, the camera 2 may transmit, to the excrement determination device 3, image data captured in the period from the time point when the excreter sits on the toilet seat 102 to the time point when the excreter leaves the toilet seat 102. However, this is a mere example, and the camera 2 may always transmit captured image data to the excrement determination device 3.

The sitting sensor 4 is arranged in the sensor unit 105 to detect whether the excreter sits on the toilet seat 102. The sitting sensor 4 includes an illuminance sensor which detects an illuminance of a periphery of the bowl 101a, and a distance measurement sensor which detects a distance to a certain object at the periphery of the bowl 101a. When the excreter sits on the toilet seat 102, the opening section is closed by the buttocks thereof. Therefore, the periphery of the bowl 101a gets dark. This means that an object exists in the vicinity of the sensor unit 105. In this way, use of the illuminance sensor and the distance measurement sensor leads to achievement of detecting whether the excreter sits on the toilet seat 102. The sitting sensor 4 may include a pressure sensor which detects a pressure of the excreter on the toilet seat 102, in place of the illuminance sensor and the distance measurement sensor. Alternatively, the sitting sensor 4 may include either the illuminance sensor or the distance measurement sensor.

The excrement determination device 3 is arranged, for example, on a side surface of the water reservoir tank 103. The excrement determination device 3 may be arranged in any position in the toilet room without limitation to the aforementioned arrangement position. Further, in a configuration where the sensor unit 105 and the excrement determination device 3 are wirelessly connected to each other, the excrement determination device 3 may not be arranged in the toilet room, and may be arranged in other place as long as the wireless communication with the sensor unit 105 is available.

The excrement determination device 3 includes a processor 31, a memory 32, and a communication part 33. For instance, the memory 32 includes a storage device, such as a RAM (Random Access Memory) and an SSD (Solid State Drive) or a flash memory, for storing various kinds of information. The memory 32 stores the sensing data transmitted by the first gas sensor 1.

For instance, the processor 31 includes a center processing unit (CPU) or an ASIC (application specific integrated circuit). The processor 31 includes a sensing data acquisition part 311, an image data acquisition part 312, an excrement determination part 313, a determination result output part 314, and a sitting determination part 315.

The sensing data acquisition part 311 acquires the sensing data indicating the hydrogen concentration at the periphery of the toilet 101 as detected by the first gas sensor 1. The sensing data acquisition part 311 reads out sensing data stored in the memory 32.

The image data acquisition part 312 acquires the image data captured by the camera 2.

The excrement determination part 313 determines whether the hydrogen concentration indicated by the sensing data is higher than a first reference concentration (first determination). It has been found that a hydrogen concentration acquired on an occurrence of flatulating is higher than a hydrogen concentration acquired on a sole occurrence of defecation Hence, under setting of the first reference concentration based on a detection result of a hydrogen concentration at defecation solely occurred by a certain excreter, it is determined that at least one of the defecation and the flatulating occurred by the excreter when the hydrogen concentration detected by the first gas sensor 1 is equal to or higher than the first reference concentration. In this regard, the first reference concentration takes a predetermined value based on the detection result of the hydrogen concentration at the defecation solely occurred by the excreter. However, this is a mere example, and the first reference concentration may take a predetermined value based on the detection result of the hydrogen concentration at flatulating occurred by the excreter.

The excrement determination part 313 executes image processing onto the image data and determines whether the image data contains a defecation image about defecation (second determination). The contents of the image processing will be described later. The excrement determination part 313 determines, based on a determination result of the first determination and a determination result of the second determination, that at least one of the defecation and the flatulating occurred (third determination).

Here, it is determined in the third determination that both the defecation and the flatulating occurred when the determination result of the first determination shows that the hydrogen concentration is higher than the first reference concentration and the determination result of the second determination shows that the image data contains a defecation image. Moreover, it is determined in the third determination that the flatulating solely occurred when the determination result of the first determination shows that the hydrogen concentration is higher than the first reference concentration and the determination result of the second determination shows that the image data does not contain the defecation image.

The excrement determination part 313 determines, based on the image data, whether the urination or the defecation occurred when the determination result of the first determination shows that the hydrogen concentration detected by the first gas sensor 1 is equal to or lower than the first reference concentration (fourth determination).

The determination result output part 314 generates excretion history information including the determination result of the third determination or a determination result of the fourth determination and transmits the generated excretion history information to the server 6 via the communication part 33, and then the memory 32 stores the excretion history information. The excretion history information may include daily time about indicating a date and time when excretion (defecation, flatulating, urination, and a combination of defecation and flatulating) occurred. The excretion history information may further include identification information of the excreter. Moreover, the excretion history information may include the hydrogen concentration detected by the first gas sensor 1. Furthermore, the excretion history information may include the image data captured by the camera 2. For instance, when the toilet 101 is provided in an individual room of a care receiver, the care receiver can be identified from the room number of the care receiver. In this case, the identification information of the room provided with the excrement determination device 3 is adopted as the identification information of the excreter.

The sitting determination part 315 determines, based on a detection result from the sitting sensor 4, whether the excreter sits on the toilet seat 102. For instance, the sitting determination part 315 may determine that the excreter sits on the seat when the illuminance detected by the illuminance sensor of the sitting sensor 4 is smaller than a reference illuminance and a distance to the object detected by the distance measurement sensor of the sitting sensor 4 is shorter than a reference distance. However, this is a mere example, and the sitting determination part 315 may determine that the excreter sits on the toilet seat 102 by using the detection result from either the illuminance sensor or the distance measurement sensor, or may determine that the excreter sits on the toilet seat 102 when the pressure detected by the pressure sensor is equal to or larger than the reference pressure.

The communication part 33 includes a communication circuit connecting the excrement determination device 3 to a network 5. The communication part 33 transmits the excretion history information to the server 6. The excrement determination device 3 is communicably connected to the server 6 via the network 5. The network 5 includes, for example, the internet. The server 6 receives the excretion history information transmitted by the excrement determination device 3. The server 6 includes a database for storing the excretion history information.

For instance, a caregiver uses the database in the server 6 when creating monitoring data of a care receiver. Specifically, a terminal device used by the caregiver acquires from the server 6 the excretion history information and the daily time information corresponding to the identification information of the care receiver to create the monitoring data of the care receiver. For example, the terminal device may create the monitoring data based on a frequency of flatulating in a predetermined period, a frequency of defecation in the predetermined period, a frequency of urination in the predetermined period, and a frequency of a combination of defecation and flatulating in the predetermined period. The predetermined period for the creation of the monitoring data may be one day, one week, or one month. For instance, the terminal device may create the monitoring data based on a time of each flatulating, defecation, urination, and each combination of defecation and flatulating in the predetermined period.

Figure 3:
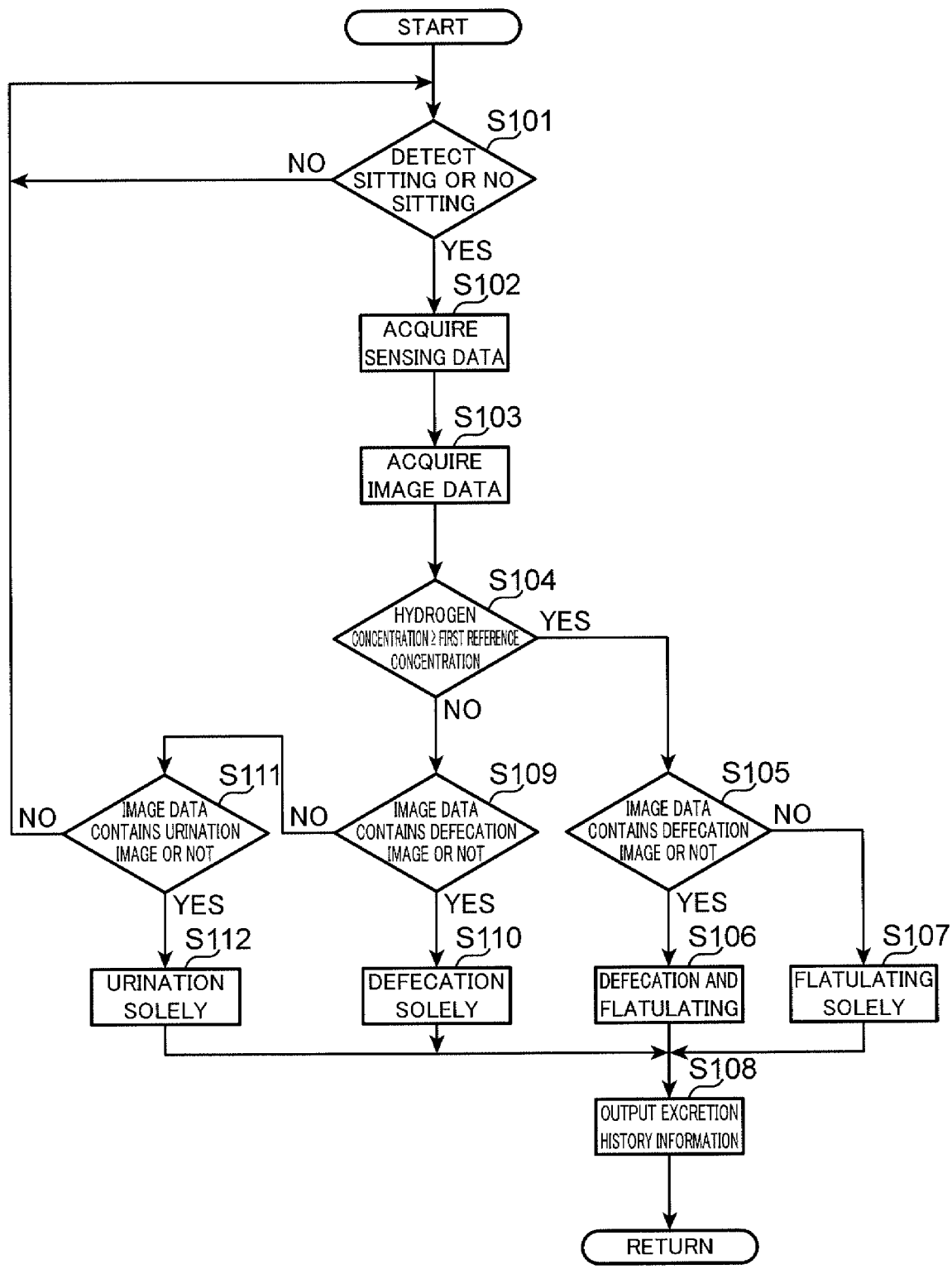
FIG. 3 is a flowchart of an excrement determination process in the first embodiment of the disclosure.

Next, an excrement determination process by the excrement determination device 3 in the first embodiment of the disclosure will be described. FIG. 3 is a flowchart of the excrement determination process in the first embodiment of the disclosure. In step S101, the sitting determination part 315 determines, based on a detection result from the sitting sensor 4, whether an excreter sits on the toilet 101. When it is determined that the excreter does not sit (NO in step S101), the process stays in step S101. Contrarily, when it is determined that the excreter sits (YES in step S101), the process proceeds to step S102.

In step S102, the sensing data acquisition part 311 acquires, from the first gas sensor 1, sensing data indicating a hydrogen concentration detected by the first gas sensor 1. In step S103, the image data acquisition part 312 acquires, from the camera 2, image data captured by the camera 2.

In step S104, the excrement determination part 313 determines whether the hydrogen concentration indicated by the sensing data acquired in step S102 is equal to or higher than the first reference concentration (first determination). When it is determined that the hydrogen concentration is equal to or higher than the first reference concentration (YES in step S104), the process proceeds to step S105. When it is determined that the hydrogen is lower than the first reference concentration (NO in step S104), the process proceeds to step S109.

In step S105, the excrement determination part 313 determines whether the image data acquired in step S103 contains a defecation image (second determination).

Here, the excrement determination part 313 may determine whether the image data contains the defecation image, for example, in a manner described below. First, the excrement determination part 313 calculates difference image data indicating a difference between the image data acquired in step S103 and base image data. The base image data represents image data generated through calibration executed in arrangement of the sensor unit 105 to the toilet 101. The base image data is generated, for example, based on a plurality of pieces of color image data obtained by capturing images of the state of the bowl 101a without defecation and urination by the camera 2 a plurality of times. In other words, the base image data represents color image data obtained in a default state of the bowl 101a without defecation and urination. Therefore, image data about defecation or urination is extractable by taking a difference between the base image data and the image data captured at the defecation or the urination. Subsequently, the excrement determination part 313 calculates an RGB ratio among an R component, a G component, and a B component contained in the calculated difference image data. Then, the excrement determination part 313 calculates a distance between the calculated RGB ratio and a predetermined defecation reference ratio. The RGB ratio represents, for example, a ratio among a total value of the luminance of the R component, a total value of the luminance of the G component, and a total value of the luminance of the B component, in the difference image data. The defecation reference ratio represents a typical defecation RGB ratio calculated by analyzing a plurality of pieces of image data containing various defecation images. For instance, the Euclidean distance is adopted for the distance. The excrement determination part 313 finally determines that the image data captured by the camera 2 contains a defecation image when the calculated distance is equal to or shorter than the reference distance.

When it is determined in step S105 that the image data contains the defecation image (YES in step S105), the excrement determination part 313 determines that both the defecation and the flatulating occurred (step S106).

Contrarily, when it is determined in step S105 that the image data does not contain the defecation image (NO in step S105), the excrement determination part 313 determines that the flatulating solely occurred (step S107).

In step S109, the excrement determination part 313 determines whether the image data contains a defecation image (fourth determination). When it is determined that the image data contains the defecation image (YES in step S109), the excrement determination part 313 determines that the defecation solely occurred (step S110). The details of the step for determining whether the image data contains the defecation image are the same as those of step S105 described above.

Contrarily, when it is determined that the image data does not contain the defecation image (NO in step S109), the excrement determination part 313 determines whether the image data contains a urination image about urination (fourth determination).

The excrement determination part 313 may determine whether the image data contains the urination image, for example, in a manner described below. First, the excrement determination part 313 calculates difference image data between the image data acquired in step S103 and the base image data. Subsequently, the excrement determination part 313 calculates an RGB ratio of the difference image data.

Then, the excrement determination part 313 calculates a distance between the calculated RGB ratio and a predetermined urination reference ratio. The predetermined urination reference ratio represents a typical urination RGB ratio calculated by analyzing a plurality of pieces of image data containing various urination images. The excrement determination part 313 may finally determine that the image data acquired in step S103 contains the urination image when the calculated distance is equal to or shorter than the reference distance.

When it is determined in step S111 that the image data acquired in step S103 contains the urination image (YES in step S111), the excrement determination part 313 determines that the urination solely occurred (step S112). Contrarily, when it is determined that the image data acquired in step S103 does not contain the urination image (NO in step S111), no excretion occurred, and thus the process returns to step S101.

The process having undergone steps S106, S107, S110, and S112 proceeds to step S108. In step S108, the determination result output part 314 transmits excretion history information including a determination result in step S105, S109, or S111 to the server 6 via the communication part 33.

For instance, when a determination result of the flatulating is obtained (step S107), generated is excretion history information associating the determination result of the flatulating, daily time information about a date and time when the flatulating occurred, a hydrogen concentration at the determination, and identification information with one another. For instance, when a determination result of defecation and flatulating is obtained (step S106), generated is excretion history information associating the determination result of the defecation and flatulating, daily time information about a date and time when the defecation and flatulating occurred, a hydrogen concentration at the determination, and identification information with one another. For example, when it is determined that the defecation solely occurred (step S110), generated is excretion history information associating the determination result of the defecation, daily time information about a date and time when the defecation solely occurred, a hydrogen concentration at the determination, and identification information with one another. For instance, when it is determined that the urination occurred (step S112), generated is excretion history information associating the determination result of the urination, daily time information indicating a date and time when the urination occurred, a hydrogen concentration at the determination, and identification information with one another.

When step S108 is finished, the process returns to step S101. The server 6 having received the excretion history information stores the received excretion history information as the excretion history information in the database.

As described above, according to the embodiment, it is determined that defecation and flatulating occurred when a determination result of the second determination shows that the image data contains a defecation image and a determination result of the first determination shows that a hydrogen concentration detected by the first gas sensor 1 is higher than the first reference concentration. This configuration therefore enables an accurate determination on the occurrence of the defecation accompanied by the flatulating.

Besides, according to the embodiment, it is determined that flatulating solely occurred when the determination result of the first determination shows that the hydrogen concentration detected by the first gas sensor 1 is higher than the first reference concentration and the determination result of the second determination shows that the image data does not contain the defecation image. This configuration therefore enables an accurate determination on the sole occurrence of the flatulating.

Moreover, in this configuration, the first gas sensor 1 has a sensitivity to hydrogen, and therefore enables an accurate determination on the occurrence of at least one of defecation and flatulating occurred even for a person who generates no odor at the defecation or the flatulating.

In addition, it is determined, based on the image data, whether defecation or urination occurred when the first gas sensor 1 fails to detect a hydrogen concentration which is equal to or higher than the first reference concentration. This configuration therefore achieves detection of urination which is less detectable by the first gas sensor 1.

Second Embodiment

Figure 4:
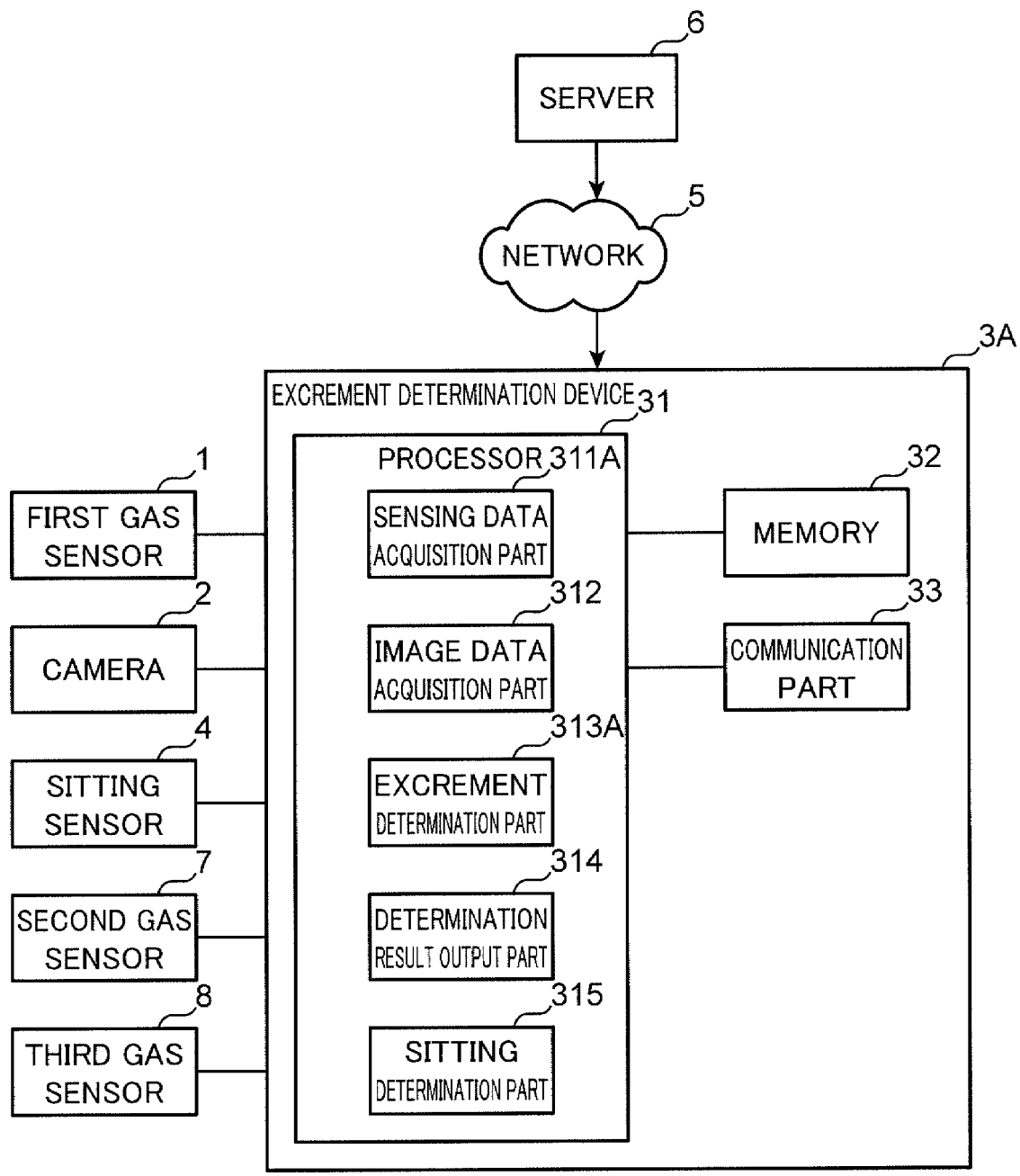
FIG. 4 shows a configuration of an excretion management system in a second embodiment of the disclosure.

FIG. 4 shows a configuration of an excretion management system in a second embodiment of the disclosure. The second embodiment has a feature in that the excretion management system further includes a second gas sensor 7 and a third gas sensor 8. In the second embodiment, elements which are the same as those in the first embodiment are given the same reference numerals, and thus explanation therefor will be omitted. Moreover, in FIG. 4, a block having operability different from that of a corresponding block in the first embodiment is given the alphabet "A" at the end of the same reference numeral.

The second gas sensor 7 has a sensitivity to ammonia. The second gas sensor 7 may transmit, to an excrement determination device 3A, sensing data indicating an ammonia concentration as detected in a period from a time point when an excreter sits on a toilet seat 102 to a time point when the excreter leaves the toilet seat 102. However, this is a mere example, and the second gas sensor 7 may always transmit, to the excrement determination device 3A, the sensing data indicating the detected ammonia concentration.

The third gas sensor 8 has a sensitivity to hydrogen sulfide. The third gas sensor 8 may transmit to the excrement determination device 3A, sensing data indicating a hydrogen sulfide concentration as detected in the period from the time point when the excreter sits on the toilet seat 102 to the time point when the excreter leaves the toilet seat 102. However, this is a mere example, and the third gas sensor 8 may always transmit, to the excrement determination device 3A, the sensing data indicating a detected hydrogen sulfide concentration.

The second gas sensor 7 and the third gas sensor 8 are arranged, for example, in a sensor unit 105. The second gas sensor 7 and the third gas sensor 8 are communicably connected to the excrement determination device 3A through a wired or wireless communication.

A sensing data acquisition part 311A acquires, in addition to sensing data from a first gas sensor 1, the sensing data indicating the ammonia concentration at the periphery of a toilet 101 as detected by the second gas sensor 7 and the sensing data indicating the hydrogen sulfide concentration at the periphery of the toilet 101 as detected by the third gas sensor 8.

An excrement determination part 313A differs from the corresponding one of the first embodiment 1 in a fourth determination. Specifically, the excrement determination part 313A determines, based on the ammonia concentration detected by the second gas sensor 7, whether urination solely occurred (fourth determination) when the hydrogen concentration detected by the first gas sensor 1 is equal to or lower than a first reference concentration. The excrement determination part 313A further determines, based on the hydrogen sulfide concentration detected by the third gas sensor 8, whether defecation solely occurred when the hydrogen concentration detected by the first gas sensor 1 is equal to or lower than the first reference concentration.

Figure 5:
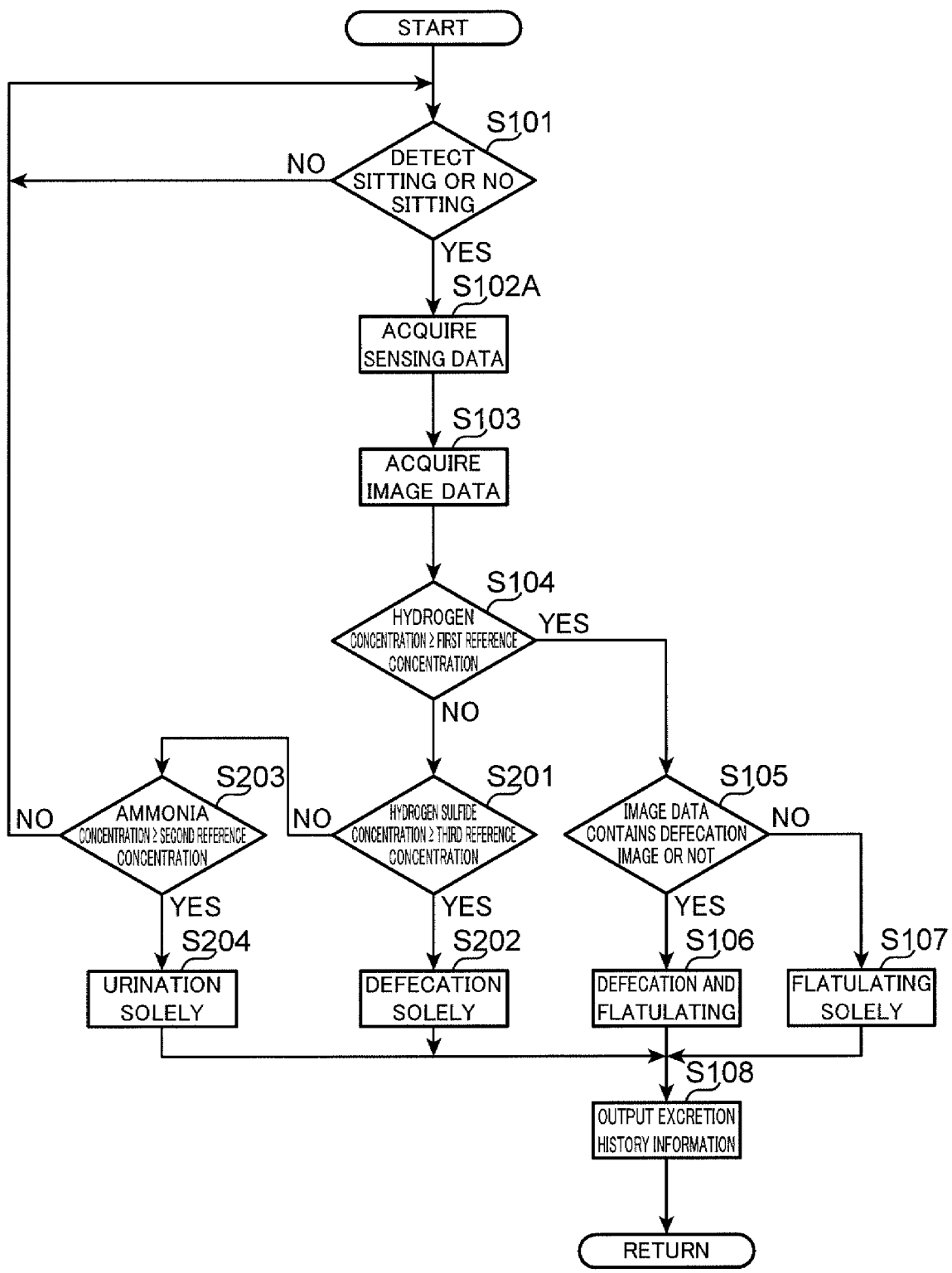
FIG. 5 is a flowchart of an excrement determination process in the second embodiment of the disclosure.

Next, an excrement determination process by the excrement determination device 3A in the second embodiment of the disclosure will be described. FIG. 5 is a flowchart of the excrement determination process in the second embodiment of the disclosure. Here, in the flowchart, elements which are the same as those in the first embodiment are given the same reference numerals, and thus explanation therefor will be omitted.

In step S102A, the sensing data acquisition part 311A acquires sensing data from each of the first gas sensor 1, the second gas sensor 7, and the third gas sensor 8.

In step S201 subsequent to step S104, the excrement determination part 313A determines whether a hydrogen sulfide concentration detected by the third gas sensor 8 is equal to or higher than a third reference concentration. The third reference concentration takes a predetermined value based on, for example, a detection result of the hydrogen sulfide concentration at defecation solely occurred by the excreter.

When it is determined that the hydrogen sulfide concentration is equal to or higher than the third reference concentration (YES in step S201), the excrement determination part 313A determines that the defecation solely occurred (step S202). Contrarily, when it is determined that the hydrogen sulfide concentration is lower than the third reference concentration (NO in step S201), the process proceeds to step S203.

In step S203, the excrement determination part 313A determines whether an ammonia concentration detected by the second gas sensor 7 is equal to or higher than a second reference concentration. When it is determined that the ammonia concentration is equal to or higher than the second reference concentration (YES in step S203), the excrement determination part 313A determines that urination solely occurred (step S204). The second reference concentration takes a predetermined value based on, for example, a detection result of the ammonia concentration at urination solely occurred by the excreter. Contrarily, when it is determined that the ammonia concentration is lower than the second reference concentration, no excretion has occurred, and thus the process returns to step S101. The process having undergone steps S202 and S204 proceeds to step S108.

As described heretofore, according to the second embodiment, when the first gas sensor 1 fails to detect hydrogen having a concentration which is equal to or higher than the first reference concentration, it is determined whether urination occurred, based on an ammonia concentration detected by the second gas sensor 7 for detecting ammonia and a hydrogen sulfide concentration detected by the third gas sensor 8 for detecting hydrogen sulfide. This configuration therefore achieves detection of urination which is less detectable by the first gas sensor 1.

In addition, according to the second embodiment, the camera 2 is activated only when the first determination is affirmative (YES in step S104), and thus power consumption is reducible.

Third Embodiment

Figure 6:
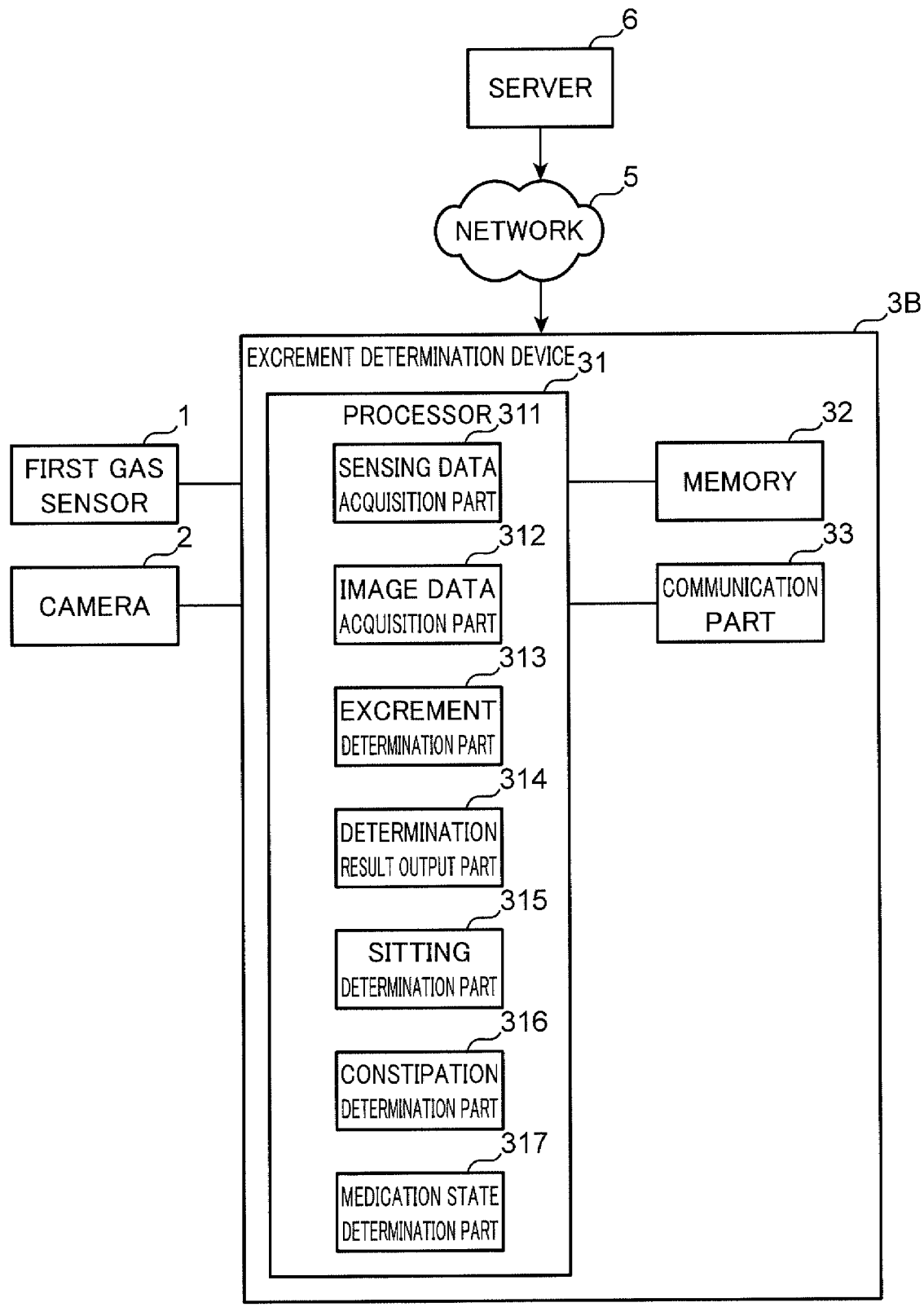
FIG. 6 is a block diagram showing a configuration of an excretion management system in a third embodiment of the disclosure.

FIG. 6 is a block diagram showing a configuration of an excretion management system in a third embodiment of the disclosure. The third embodiment is based on the first embodiment, and has a feature in that a processor 31 further includes a constipation determination part 316 and a medication state determination part 317. In the third embodiment, elements which are the same as those in the first embodiment are given the same reference numerals, and thus explanation therefor will be omitted.

The constipation determination part 316 reads out excretion history information from a memory 32 per excreter, determines whether an increase rate of a hydrogen concentration indicated by the read excretion history information is equal to or larger than a second threshold when the excretion history information shows that a defecation interval of the excreter is equal to or larger than a first threshold and that flatulating has occurred continuously in the defecation interval, and further determines that the excreter has constipation when it is determined that the increase rate is equal to or larger than the second threshold.

The medication state determination part 317 calculates, based the excretion history information stored in the memory 32, an increase rate of a hydrogen concentration, and determines, based on whether the calculated increase rate is equal to or larger than a third threshold, a medication state of the excreter. The medication state represents a state whether or not the excreter appropriately takes a medicine prescribed therefor. For instance, it has been found that suspension of the intake of the medicine, such as an antibiotic or a laxative, by the excreter results in an increase in a concentration of hydrogen discharged from the inside of the body when at least one of the defecation and the flatulating occurred. In this respect, monitoring of the hydrogen concentration concerning the excreter leads to a successful determination on the medication state of the excreter.

Figure 7:
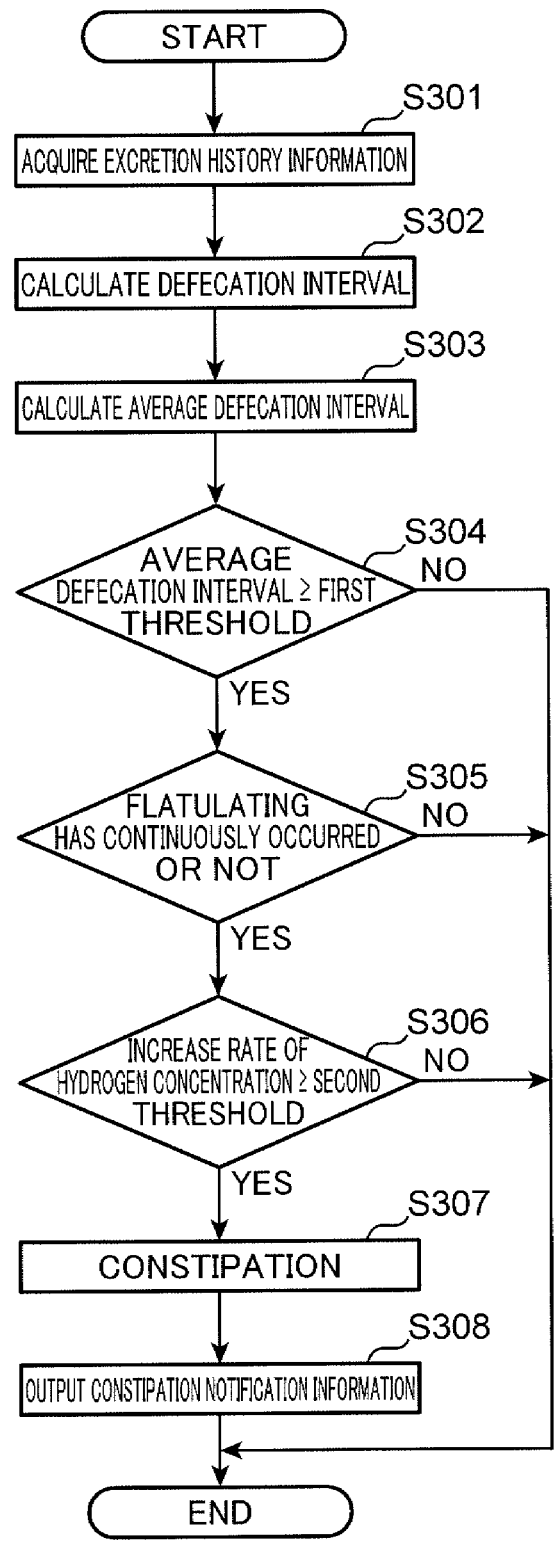
FIG. 7 is a flowchart of a constipation determination process in the third embodiment of the disclosure.

FIG. 7 is a flowchart of a constipation determination process in the third embodiment of the disclosure. The process in the flowchart may be periodically (e.g., per day, per week, per month) executed, or may be executed when an amount of the excretion history information about the excreter as stored in the memory 32 increases by a predetermined value since previous execution of the process. In step S301, the constipation determination part 316 acquires, based on identification information, excretion history information from the memory 32 per excreter. Here, the constipation determination part 316 may acquire the excretion history information in a given period from a specific current time point to a specific past time point. Hereinafter, the constipation determination process for a specific excreter will be described.

In step S302, the constipation determination part 316 calculates, based on the excretion history information, a defecation interval of the excreter. Here, the constipation determination part 316 extracts, from among read excretion history information, excretion history information indicating that excretion includes defecation solely, and excretion history information indicating that the excretion includes defecation and flatulating. Then, the constipation determination part 316 calculates the defecation interval by applying, to all the extracted excretion history information, a process of calculating a difference between daily times indicated by daily time information respectively included in two pieces of excretion history information, i.e., chronologically preceding excretion history information and chronologically subsequent excretion history information. In this manner, chronological data about defecation intervals is obtained.

In step S303, the constipation determination part 316 calculates an average defecation interval representing an average value of the defecation intervals.

In step S304, the constipation determination part 316 determines whether the average defecation interval is equal to or larger than a first threshold. When the average defecation interval is equal to or larger than the first threshold (YES in step S304), the constipation determination part 316 determines whether flatulating has continuously occurred (step S305).

For instance, the constipation determination part 316 extracts excretion history information about excretion including the flatulating solely in each of the defecation intervals. Then, the constipation determination part 316 calculates, based on the extracted excretion history information, a frequency of flatulating in each of the defecation intervals. Next, the constipation determination part 316 extracts a defecation interval having a predetermined or larger frequency (predetermined value of two or more) of the flatulating among all the defecation intervals. Subsequently, the constipation determination part 316 determines that the flatulating has continuously occurred when there is a predetermined or larger number of extracted defecation intervals. Contrarily, the constipation determination part 316 determines that the flatulating has not continuously occurred in a case of no defecation interval having the predetermined or larger frequency of the flatulating, or in a case of fewer flatulating intervals than the predetermined number, each of the flatulating intervals having the predetermined or larger frequency of the flatulating.

When it is determined that the flatulating has continuously occurred (YES in step S305), the constipation determination part 316 determines whether an increase rate of the hydrogen concentration is equal to or larger than the second threshold (step S306). For instance, the constipation determination part 316 may calculate an increase rate of the hydrogen concentration from the hydrogen concentration indicated by the excretion history information read out in step S301 in a given period from a specific current time point to a specific past time point, and determine that the hydrogen concentration has increased by the second threshold or larger when the calculated increase rate is equal to or larger than the second threshold. Details of the increase rate will be explained in description about a medication state determination process to be described later.

When it is determined that the increase rate of the hydrogen concentration is equal to or larger than the second threshold (YES in step S306), the constipation determination part 316 determines that the excreter has constipation (step S307).

In step S308, the constipation determination part 316 generates constipation notification information indicating that the excreter has the constipation, and outputs the constipation notification information via the communication part 33. In this case, the constipation determination part 316 may transmit the constipation notification information to, for example, a terminal device owned by a manager of the excreter. Examples of the manager of the excreter include a caregiver and a family member of the excreter.

Figure 8:
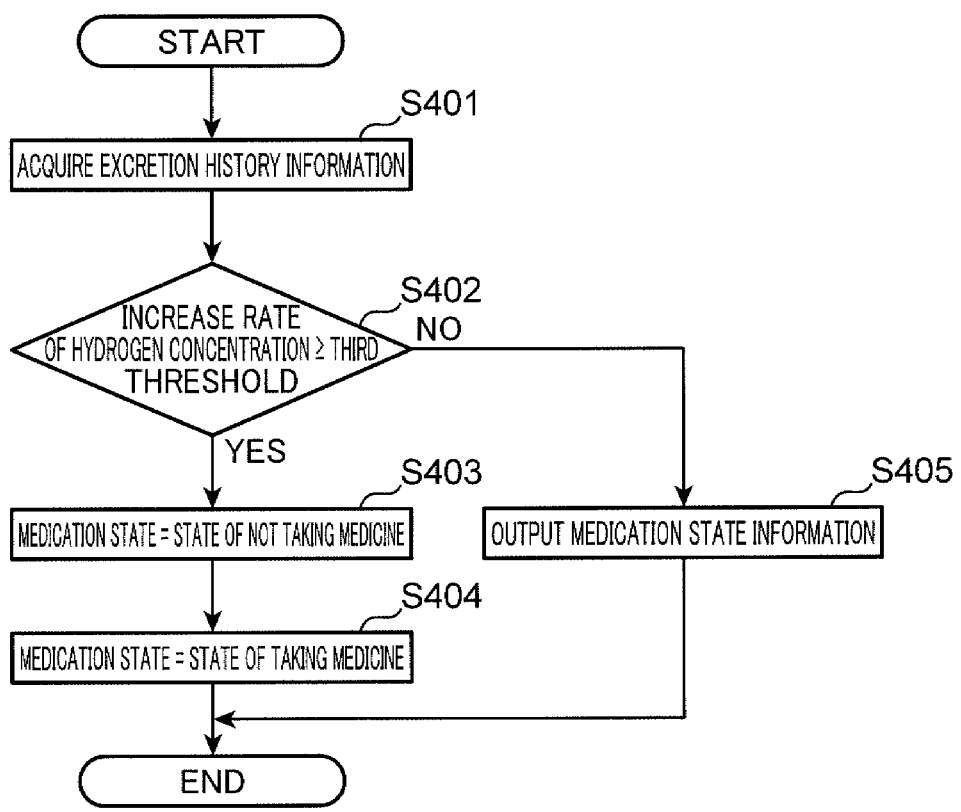
FIG. 8 is a flowchart of a medication state determination process in the third embodiment of the disclosure.

Subsequently, a determination on a medication state will be described. FIG. 8 is a flowchart of a medication state determination process in the third embodiment of the disclosure. The process in the flowchart may be periodically (e.g., per day, per week, per month) executed, or may be executed when an amount of the excretion history information about a user as stored in the memory 32 increases by a predetermined value since previous execution of the process.

In step S401, the excretion history information is acquired, based on identification information, from the memory 32 per excreter. Here, the meditation state determination part 317 may acquire the excretion history information in a given period from a specific current time point to a specific past time point. Hereinafter, a medication state determination process for a specific excreter will be described.

In step S402, the medication state determination part 317 determines whether an increase rate of the hydrogen concentration is equal to or larger than a third threshold. Here, the medication state determination part 317 may calculate, as the increase rate, a value obtained by subtracting a hydrogen concentration indicated by the oldest excretion history information from a hydrogen concentration indicated by the latest hydrogen concentration, among the excretion history information acquired in step S401.

Alternatively, the medication state determination part 317 may calculate, as the increase rate, a value obtained by subtracting an average value of hydrogen concentrations indicated by the excretion history information including the oldest one in a second period from an average value of hydrogen concentrations indicated by the excretion history information including the latest one in a first period. The first period corresponds to, for example, a given period (e.g., one week, two weeks, and one month) from the latest time toward the past. The second period corresponds to a given period (e.g., one week, two weeks, and one month) from the oldest time point toward the present.

Alternatively, the medication state determination part 317 calculates an increase value of the hydrogen concentration by subtracting a hydrogen concentration indicated by chronologically preceding excretion history information from a hydrogen concentration indicated by chronologically subsequent excretion history information, among the extracted excretion history information. Then, the medication state determination part 317 may apply the process of calculating the increase value of the hydrogen concentration to all the excretion history information acquired in step S401, calculate an integrated value by accumulating a plurality of calculated increase values, and may calculate the calculated integrated value as the increase rate. The increase value takes a minus value when the hydrogen concentration indicated by the chronologically subsequent excretion history information is lower than the hydrogen concentration indicated by the chronologically preceding excretion history information.

When it is determined that the increase rate of the hydrogen concentration is equal to or larger than the third threshold (YES in step S402), the medication state determination part 317 determines that the excreter is in a medication state of failing to take a medicine (in a non-medication state) (step S403).

In step S404, the medication state determination part 317 generates medication state information indicating that the excreter fails to take the medicine, and outputs the generated medication state information. Here, the medication state determination part 317 may transmit the generated medication state information to a terminal device owned by a manager of the excreter via the communication part 33. Consequently, the manager can recognize that the excreter fails to take the medicine and appropriately encourage the excreter to take the medicine.

Contrarily, when it is determined that the increase rate of the hydrogen concentration is smaller than the third threshold (NO in step S402), the medication state determination part 317 determines that the excreter is in a medication state of taking the medicine (step S405). When it is determined that the excreter takes the medicine, the intake of the medicine proceeds without any problem, and therefore, the process is finished without generating medication state information. However, this is a mere example. The medication state determination part 317 may generate medication state information indicating the medication state of taking the medicine, and transmit the generated medication state information to the terminal device. Consequently, the manager of the excreter can confirm that the excreter takes the medicine.

As described heretofore, according to the embodiment, a determination on the constipation is made, when it is specified from the excretion history information that a defecation interval is equal to or larger than the first threshold and that flatulating has continuously occurred in the defection interval, and further when an increase rate of the hydrogen concentration changes by the second threshold or larger. This configuration therefore enables an accurate determination on the constipation.

Moreover, according to the embodiment, the increase rate of the hydrogen concentration is calculated, based on the excretion history information, and the medication state of the excreter is determined, based on whether the increase rate is equal to or larger than the third threshold. This configuration therefore achieves an accurate determination on the medication state of intake or no intake of a medicine by the excreter.

This disclosure can adopt modifications described below.

(1) The constipation determination part 316 and the medication state determination part 317 may be provided in the server 6. In this case, the constipation determination part 316 provided in the server 6 may determine constipation or no constipation by using the excretion history information stored in the database of the server 6. Besides, the medication state determination part 317 provided in the server 6 may determine a medication state by using the excretion history information stored in the database of the server 6.

(2) Although the medication state determination part 317 determines, based on the hydrogen concentration, a medication state, this is a mere example, and the medication state determination part may determine, based on a hydrogen sulfide concentration or an ammonia concentration, the medication state. Details of a determination process of a medication state based on the hydrogen sulfide concentration or the ammonia concentration are the same as those for the determination process of the medication state based on the hydrogen concentration. Moreover, the medication state determination part 317 may determine a medication state based on each of the hydrogen concentration, the hydrogen sulfide concentration, and the ammonia concentration, and determine that an excreter is in a medication state of failing to take a medicine when at least one determination result indicates a non-medication state.

(3) The first threshold used for a determination on a defecation interval may take a different value per excreter. In this case, a manager may determine an appropriate value for the first threshold in view of a past defecation interval of the excreter, input the determined first threshold to the excrement determination device 3 by using a manipulation device (not shown), and then set the first threshold. Alternatively, the constipation determination part 316 may calculate, based on the excretion history information, a defecation interval in a given past period for the excreter, and set, based on the calculated defecation interval, the first threshold.

(4) The second threshold used for a determination on an increase rate by the constipation determination part 316 may take a different value per excreter. In this case, a manager may determine a value for the second threshold, based on a past increase tendency (e.g., increase rate) of the hydrogen concentration about the excreter, input the determined second threshold to the excrement determination device 3 by using a manipulation device (not shown), and then set the second threshold. Alternatively, the constipation determination part 316 may calculate, based on the excretion history information, an increase rate of the hydrogen concentration in a given past period for the excreter, and set, based on the calculated increase rate, the second threshold. Further alternatively, the first reference concentration may be adopted for the second threshold.

(5) The third threshold used for a determination on an increase rate of a hydrogen concentration by the medication state determination part 317 may take a different value per excreter. In this case, a manager may determine a value for the third threshold, based on an increase rate of the hydrogen concentration about the excreter in a state of taking a medicine, input the determined third threshold to the excrement determination device 3 by using a manipulation device (not shown), and then set the third threshold. Alternatively, the medication state determination part 317 may calculate, based on the excretion history information, an increase rate of the hydrogen concentration about the excreter in the state of taking the medicine, and set, based on the calculated increase rate, the third threshold. This is applicable to the determination process for the medication state in use of hydrogen sulfide or ammonia in place of the hydrogen.

(6) Although steps S102 to S107 and steps S109 to S112 are executed as shown in the flowchart in each of FIG. 3 and FIG. 5, the disclosure is not limited thereto, and steps S102 to S107 and steps S109 to S112 may be executed regardless of sitting or no sitting. In this case, steps S102 to S107 and steps S109 to S112 may be executed in a predetermined control cycle.

Figure 9:
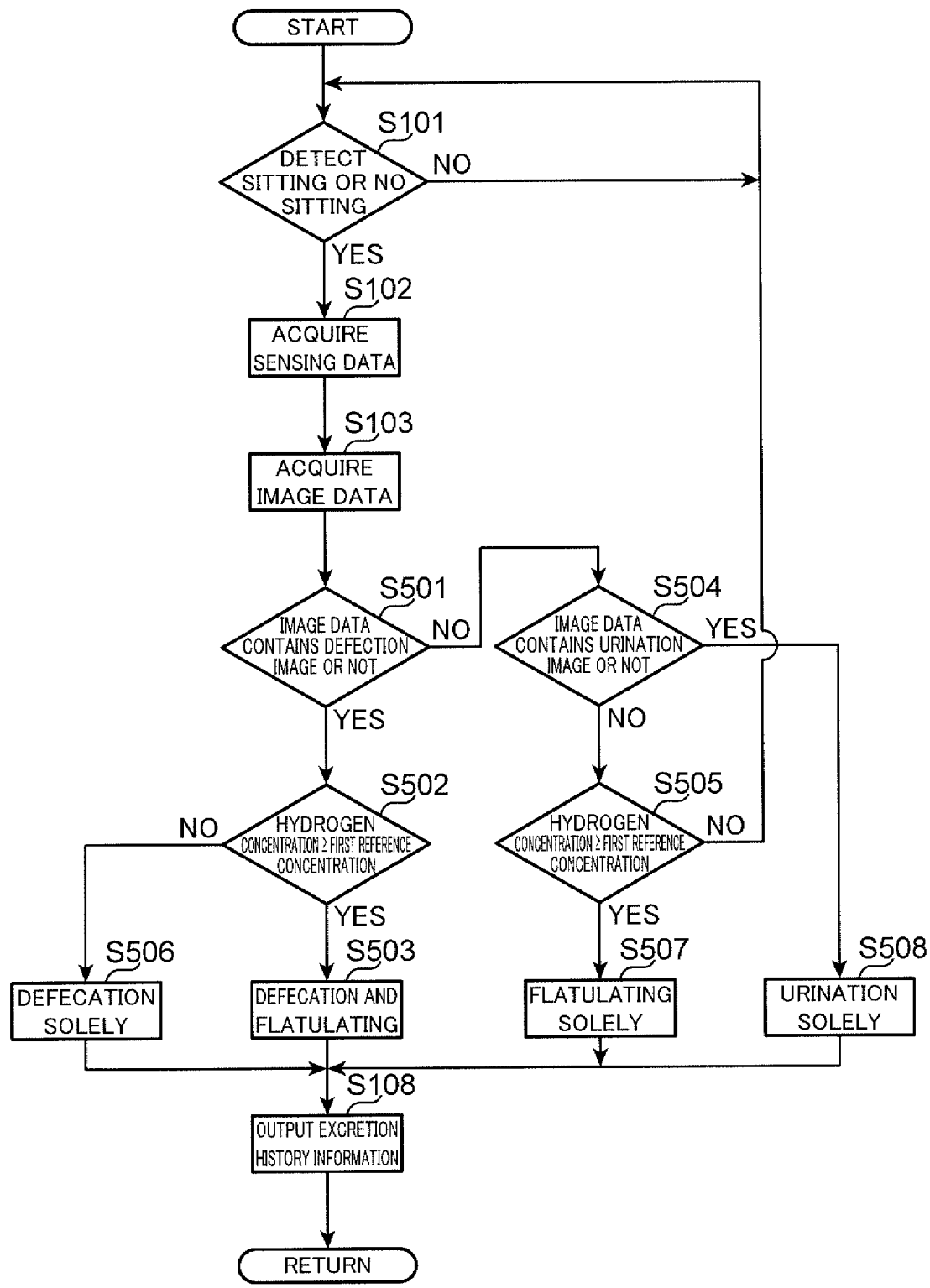
FIG. 9 is a flowchart of an excrement determination process in a modification of the disclosure.

(7) In the flowchart in each of FIG. 3 and FIG. 5, it is determined whether image data contains a defecation image (step S105) when it is determined that the determination as to whether the first hydrogen concentration is equal to or higher than the first reference concentration is affirmative (YES in step S104), but this disclosure is not limited thereto. For example, a flowchart shown in FIG. 9 may be adopted. The flowchart in FIG. 9 shows an excrement determination process in a modification of the disclosure. This flowchart has a feature in performing a determination on image data prior to determination on a hydrogen concentration. In the flowchart, steps which are the same as those in FIG. 3 and FIG. 5 are given the same reference numerals, and thus explanation therefor will be omitted.

In step S501 subsequent to step S103, an excrement determination part 313 determines whether image data contains a defecation image. When it is determined that the image data contains the defecation image (YES in step S501), the excrement determination part 313 determines whether a hydrogen concentration is equal to or higher than a first reference concentration (step S502). When it is determined that the hydrogen concentration is equal to or higher than the first reference concentration (YES in step S502), the excrement determination part 313 determines that defecation and flatulating occurred (step S503). The set first reference concentration here takes a predetermined value based on a detection result of the hydrogen concentration at flatulating by an excreter. Contrarily, when it is determined that the hydrogen concentration is lower than the first reference concentration (NO in step S502), the excrement determination part 313 determines that defecation solely occurred (step S506).

When it is determined in step S501 that the image data does not contain the defecation image (NO in step S501), the excrement determination part 313 determines whether the image data contains a urination image (step S504).

When it is determined that the image data contains the urination image (YES in step S504), the excrement determination part 313 determines that urination solely occurred (step S508). Contrarily, when it is determined that the image data does not contain the urination image (NO in step S504), the excrement determination part 313 determines whether the hydrogen concentration is equal to or higher than the first reference concentration (step S505). When it is determined that the hydrogen concentration is equal to or higher than the first reference concentration (YES in step S505), the excrement determination part 313 determines that flatulating solely occurred (step S507). Contrarily, when it is determined that the hydrogen concentration is lower than the first reference concentration (NO in step S505), the process returns to step S101.

(8) The third embodiment is based on the first embodiment, but may be based on the second embodiment.

INDUSTRIAL APPLICABILITY

The technology according to this disclosure achieves an accurate determination as to whether at least one of flatulating and defecation occurred by an excreter, and thus is useful for determining such excrement.

The invention claimed is:

1. A method for aiding in treating constipation by notifying a terminal of a caregiver or family member that a person suffers constipation, comprising:
    detecting with a hydrogen-gas-concentration sensor sensing data indicating the concentration of hydrogen gas of flatulence from a toilet used by the person even when the flatulence is odorless;
    capturing and recording with a camera an image of a bowl of the toilet used by the person and generating with the camera image data of the image of the toilet bowl;
    acquiring with a hardware processor the sensing data of the concentration of the hydrogen gas of the flatulence from the toilet detected by the hydrogen-gas-concentration sensor;
    acquiring with the hardware processor the image data captured by the camera;
    determining with the hardware processor that the person is constipated by determining the presence of the odorless flatulence without the presence of a defecation product in the toilet bowl in response to receiving the sensing data representing a hydrogen gas concentration higher than a reference concentration, and image data from the camera indicating the absence of the defecation product in the toilet bowl; and
    outputting to the terminal with the hardware processor the determination that the person is constipated to inform the caregiver or family member of the need to obtain constipation treatment for the person.

2. The method according to claim 1, further comprising:
    determining with the hardware processor that defecation occurred and flatulence was produced when the hardware processor determines that the hydrogen gas concentration is higher than the reference concentration and the image data contains an image of the defecation product.

3. The method according to claim 1, wherein the hardware processor determines whether the image data includes an image of the defecation product when the hardware processor determines that the hydrogen gas concentration indicated by the sensing data is higher than the reference concentration.

4. The method according to claim 3, further comprising:
detecting the concentration of ammonia gas from the toilet with an ammonia gas sensor;
detecting the concentration of hydrogen sulfide gas from the toilet with a hydrogen sulfide gas sensor; and
determining with the hardware processor, based on the ammonia concentration detected by the ammonia gas sensor and the hydrogen sulfide concentration detected by the hydrogen sulfide gas sensor, whether defecation or urination occurred in the toilet when the ammonia concentration detected by the ammonia gas sensor is equal to or lower than the reference concentration.

5. The method according to claim 3, further comprising determining with the hardware processor, based on the image data, whether defecation or urination occurred in the toilet when the hardware processor determines that the hydrogen gas concentration detected by the hydrogen-gas-concentration sensor is equal to or lower than the reference concentration.

6. The method according to claim 1, wherein the hardware processor determines the presence of the odorless flatulence without the presence of a defecation product in the toilet bowl when a sitting sensor for detecting sitting of the person on the toilet detects that the person sits on the toilet.

7. The method according to claim 1, further comprising:
generating and outputting with the hardware processor excretion history information including a determination result, daily time information about a date and time when excretion occurred, and the hydrogen gas concentration, and storing with the hardware processor the excretion history information in a memory; and
determining with the hardware processor whether an increase rate of the hydrogen gas concentration indicated by the excretion history information is equal to or larger than a second threshold when the excretion history information stored in the memory indicates that a defecation interval is equal to or larger than a first threshold and indicates that the person produced flatulence continuously in the defecation interval, and determining with the hardware processor that the person has constipation when the hardware processor determines that the increase rate is equal to or larger than the second threshold.

8. The method according to claim 1, further comprising:
generating with the hardware processor excretion history information including a determination that at least one of defecation and flatulence production has occurred, daily time information about a date and time when excretion occurred, and the hydrogen gas concentration, and storing with the hardware processor the excretion history information in a memory;
calculating with the hardware processor, based on the excretion history information stored in the memory, an increase rate of the hydrogen gas concentration, and determining with the hardware processor, based on whether the increase rate is equal to or larger than a threshold, a medication state of the person; and
outputting with the hardware processor a determination result of the medication state.

9. A device for aiding in treating constipation by notifying a terminal of a caregiver or family member that a person suffers constipation, comprising:
a hydrogen-gas-concentration sensor configured to detect the concentration of hydrogen gas of flatulence from a toilet even when the flatulence is odorless;
a camera configured to record an image of a bowl of the toilet and to generate image data of the image of the toilet bowl; and
a hardware processor configured to acquire sensing data from the hydrogen-gas-concentration sensor and to acquire the image data generated by camera, wherein the hardware processor
determines the person is constipated by determining the presence of odorless flatulence without the presence of a defecation product in the toilet bowl in response to receiving sensing data representing a hydrogen gas concentration higher than a reference concentration and image data indicating the absence of the defecation product in the toilet bowl and
outputs to the terminal the determination that the person is constipated to inform the caregiver or family member of the need to obtain constipation treatment for the person.

10. A non-transitory computer-readable recording medium storing a program for causing a computer to:
acquire with a hardware processor sensing data of the concentration of hydrogen gas of odorless flatulence from a toilet produced by a person and detected by a hydrogen-gas-concentration sensor;
acquire with the hardware processor image data from a camera which is located at the toilet to capture an image of a bowl of the toilet;
determine with the hardware processor that the person is constipated by determining the presence of the odorless flatulence without the presence of a defecation product in the toilet bowl in response to
receiving sensing data from the hydrogen-gas-concentration sensor representing a hydrogen gas concentration higher than a reference concentration, and
image data from the camera indicating the absence of the defecation product in the toilet bowl; and
outputting to a terminal of a caregiver or family member of the person with the hardware processor the determination that the person is constipated to inform the caregiver or family member of the need to obtain constipation treatment for the person.

* * * * *